United States Patent
Iwakura et al.

(10) Patent No.: US 11,829,867 B2
(45) Date of Patent: Nov. 28, 2023

(54) COMPUTER-READABLE RECORDING MEDIUM AND LEARNING DATA GENERATION METHOD

(71) Applicant: FUJITSU LIMITED, Kawasaki (JP)

(72) Inventors: Satoko Iwakura, Kawasaki (JP); Shunichi Watanabe, Kawasaki (JP); Tetsuyoshi Shiota, Yokohama (JP); Izumi Nitta, Kawasaki (JP); Daisuke Fukuda, Setagaya (JP)

(73) Assignee: FUJITSU LIMITED, Kawasaki (JP)

( * ) Notice: Subject to any disclaimer, the term of this patent is extended or adjusted under 35 U.S.C. 154(b) by 1088 days.

(21) Appl. No.: 16/422,481

(22) Filed: May 24, 2019

(65) Prior Publication Data

US 2019/0378011 A1    Dec. 12, 2019

(30) Foreign Application Priority Data

Jun. 7, 2018    (JP) .................................. 2018-109392

(51) Int. Cl.
*G06N 3/08*    (2023.01)
*G06Q 10/0635*    (2023.01)
*G16H 10/60*    (2018.01)

(52) U.S. Cl.
CPC ........... *G06N 3/08* (2013.01); *G06Q 10/0635* (2013.01); *G16H 10/60* (2018.01)

(58) Field of Classification Search
None
See application file for complete search history.

(56) References Cited

U.S. PATENT DOCUMENTS

| | | | | |
|---|---|---|---|---|
| 6,219,444 B1* | 4/2001 | Shashua | ................ | G06T 15/205 348/42 |
| 2004/0030584 A1* | 2/2004 | Harris | .................... | G16H 10/60 705/3 |
| 2004/0030669 A1* | 2/2004 | Harris | .................... | G16H 40/67 |
| 2013/0036082 A1* | 2/2013 | Natarajan | .............. | G06Q 30/00 706/50 |

(Continued)

FOREIGN PATENT DOCUMENTS

JP    08329196    12/1996
JP    2006053628    2/2006

(Continued)

OTHER PUBLICATIONS

"Jen Tzung Chien, Tensor-Factorized Neural Networks, May 2018" (Year: 2018).*

(Continued)

*Primary Examiner* — Kito R Robinson
*Assistant Examiner* — Toan Duc Bui
(74) *Attorney, Agent, or Firm* — STAAS & HALSEY LLP

(57) ABSTRACT

A learning device receives, for each target, learning data that represents the source of generation of a tensor including a plurality of elements which multi-dimensionally represent the features of the target over a period of time set in advance. When the target satisfies a condition set in advance, the learning device identifies the period of time corresponding to the condition in the learning data. Subsequently, the learning device generates a weighted tensor corresponding to the learning data that is at least either before or after the concerned period of time.

6 Claims, 16 Drawing Sheets

(56) References Cited

U.S. PATENT DOCUMENTS

| | | | |
|---|---|---|---|
| 2016/0110911 A1* | 4/2016 | Frank | A61B 5/055 |
| | | | 382/131 |
| 2018/0225634 A1 | 8/2018 | Kosaka et al. | |
| 2018/0232486 A1* | 8/2018 | Carpenter | C12Q 1/6883 |
| 2019/0096525 A1* | 3/2019 | Ferenc | G16H 50/70 |
| 2019/0209022 A1* | 7/2019 | Sobol | A61B 5/6804 |
| 2020/0082264 A1* | 3/2020 | Guo | G06N 3/084 |

FOREIGN PATENT DOCUMENTS

| | | |
|---|---|---|
| JP | 2017204214 | 11/2017 |
| WO | WO2017010103 | 1/2017 |

OTHER PUBLICATIONS

"Philip Chen, A Rapid Learning and Dynamic Stepwise Updating Algorithm for Flat Neural Networks and the Application to Time-Series Prediction, Feb. 1999" (Year: 1999).*

Maruhashi, K., "Deep Tensor: Eliciting New Insights from Graph Data that Express Relationships Between People and Things" Fujitsu, Fujitsu Limited, vol. 68, Article No. 5, pp. 29-35, Sep. 1, 2017 (10 pp.).

Notification of Reason for Refusal, dated Sep. 3, 2018, in Japanese Application No. 2018109392 (7 pp.).

* cited by examiner

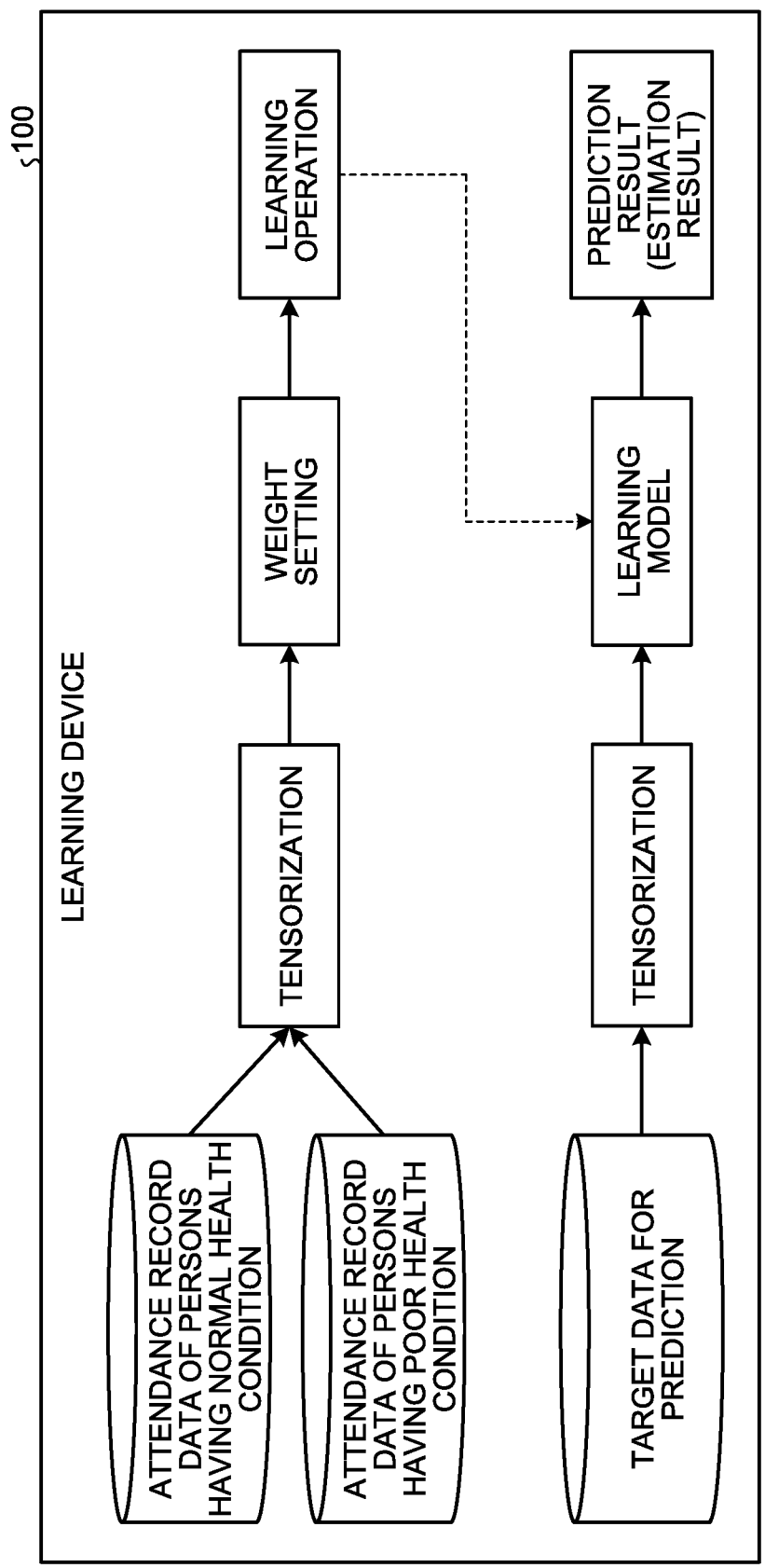

FIG.2

(a) LEARNT AS CASE OF HAVING TAKEN MEDICAL TREATMENT ("PERSON HAVING POOR HEALTH CONDITION"), LABEL (MEDICAL TREATMENT)

| MONTH | 4 | 5 | 6 | 7 | 8 | 9 | 10 | 11 | 12 |
|---|---|---|---|---|---|---|---|---|---|
| ATTENDANCE-ABSENCE | | | | ░ | ░ | ░ | ░ | | MEDICAL TREATMENT |

← PAST / PRESENT

LEAVE OF ABSENCE (×4)

(b) LEARNT AS CASE OF NOT HAVING TAKEN MEDICAL TREATMENT ("PERSON HAVING NORMAL HEALTH CONDITION"), LABEL (NO MEDICAL TREATMENT)

| MONTH | 4 | 5 | 6 | 7 | 8 | 9 | 10 | 11 | 12 |
|---|---|---|---|---|---|---|---|---|---|
| ATTENDANCE-ABSENCE | ░ | | | ░ | | | | | ░ |

← PAST / PRESENT

LEAVE OF ABSENCE

FIG.7

| EMPLOYEE NUMBER | DATE | DAY | ATTENDANCE-PRESENCE CATEGORY | CLOCK-IN TIME | CLOCK-OUT TIME | OVERTIME HOURS | BUSINESS TRIP |
|---|---|---|---|---|---|---|---|
| 100 | 04/01/2015 | WEDNESDAY | LEAVE OF ABSENCE | | | | |
| 100 | 04/02/2015 | THURSDAY | ATTENDANCE | 08:49 | 0:00 | 360 | NO |
| 100 | 04/03/2015 | FRIDAY | ATTENDANCE | 08:49 | 0:00 | 360 | NO |
| 100 | 04/04/2015 | SATURDAY | ATTENDANCE | 09:00 | 17:00 | 420 | NO |
| ... | | | | | | | |
| 100 | 08/23/2015 | TUESDAY | ATTENDANCE | 08:49 | 17:50 | 0 | NO |
| 100 | 08/24/2016 | WEDNESDAY | MEDICAL TREATMENT | | | | |
| ... | | | | | | | |
| 100 | 10/04/2016 | TUESDAY | MEDICAL TREATMENT | | | | |
| 100 | 10/02/2016 | WEDNESDAY | ATTENDANCE | 08:30 | 17:50 | 0 | NO |
| 100 | 10/03/2016 | THURSDAY | ATTENDANCE | 08:30 | 17:50 | 0 | NO |
| ... | ... | | | | | | |

FIG.8

| EMPLOYEE NUMBER | DATE | DAY | ATTENDANCE-PRESENCE CATEGORY | CLOCK-IN TIME | CLOCK-OUT TIME | OVERTIME HOURS | BUSINESS TRIP |
|---|---|---|---|---|---|---|---|
| 100 | 04/01/2015 | WEDNESDAY | LEAVE OF ABSENCE | | | | |
| 100 | 04/02/2015 | THURSDAY | ATTENDANCE | 08:49 | 0:00 | 360 | NO |
| 100 | 04/03/2015 | FRIDAY | ATTENDANCE | 08:49 | 0:00 | 360 | NO |
| 100 | 04/04/2015 | SATURDAY | ATTENDANCE | 09:00 | 17:00 | 420 | NO |
| ... | | | | | | | |
| 100 | 08/23/2015 | TUESDAY | ATTENDANCE | 08:49 | 17:50 | 0 | NO |
| 100 | 08/24/2016 | WEDNESDAY | MEDICAL TREATMENT | | | | |
| ... | | | | | | | |
| 100 | 10/04/2016 | TUESDAY | MEDICAL TREATMENT | | | | |
| 100 | 10/02/2016 | WEDNESDAY | ATTENDANCE | 08:30 | 17:50 | 0 | NO |
| 100 | 10/03/2016 | THURSDAY | ATTENDANCE | 08:30 | 17:50 | 0 | NO |
| ... | | | | | | | |

PRE-MEDICAL-TREATMENT PERIOD OF TIME (WEIGHT "1")

PERIOD OF MEDICAL TREATMENT

POST-MEDICAL-TREATMENT PERIOD OF TIME (WEIGHT "0")

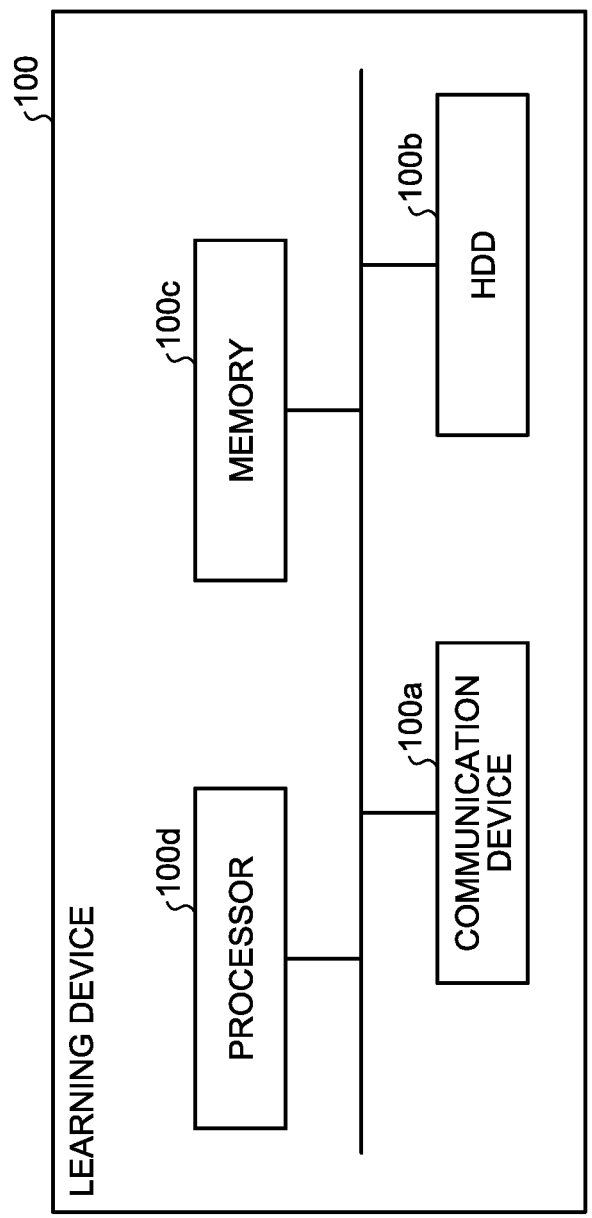

COMPUTER-READABLE RECORDING MEDIUM AND LEARNING DATA GENERATION METHOD

CROSS-REFERENCE TO RELATED APPLICATION

This application is based upon and claims the benefit of priority of the prior Japanese Patent Application No. 2018-109392, filed on Jun. 7, 2018, the entire contents of which are incorporated herein by reference.

FIELD

The embodiments discussed herein are related to a computer-readable recording medium and a learning data generation method.

BACKGROUND

A graph structure learning technology is known that enables deep learning of data of graph structures (hereinafter, a form of devices for performing such graph structure learning is called "deep tensor (DT)". In the deep tensor, a graph structure is received as the input and is treated as tensor data (hereinafter, sometimes written as a tensor). Then, in the deep tensor, a partial structure of the graph (i.e., a partial pattern of the tensor) that would contribute in performing prediction is extracted as a core tensor, thereby enabling achieving prediction of high accuracy.

Japanese Laid-open Patent Publication No. 08-329196

However, in the deep tensor mentioned above, although it is possible to process partially common patterns in the core tensor, data that is similar only in partial tensors but that actually has different features when considered in entirety gets sometimes processed as the same common pattern. That leads to deterioration in the prediction accuracy.

For example, in the case of learning attendance record data using the deep tensor, the attendance record data of persons having a poor health condition and the attendance record data of persons having a normal health condition are input to the deep tensor and a prediction model is learnt. Then, the attendance record data of the target person for determination is input to the already-learnt prediction model, and the possibility of the person taking medical treatment (taking leave of absence) is predicted.

In such learning, regarding the attendance record data of persons with medical history who have experienced taking medical treatment due to suffering from mental disorder in the past; even if those persons have resumed the normal work, sometimes the attendance record data indicates irregularity such as frequent leave of absence or frequent late arrival. In that case, the sets of attendance record data indicating irregularity in attendance, which serves as a sign of being in the stage prior to taking new medical treatment, are sometimes similar data in partial tensors. However, that does not necessarily mean that medical treatment is requested after that. Consequently, the attendance record data of the persons with medical history becomes noise and causes deterioration in the prediction accuracy regarding the persons who would newly take medical treatment.

SUMMARY

According to an aspect of an embodiment, a non-transitory computer-readable recording medium stores therein a learning data generation program that causes a computer to execute a process. The process includes receiving, for each target, learning data that represents source of generation of a tensor including a plurality of elements which multi-dimensionally represent features of the target over a period of time set in advance; identifying, when the target satisfies a condition set in advance, a period of time corresponding to the condition in the learning data; and generating a weighted tensor corresponding to the learning data that is at least either before or after the period of time.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 1 is a diagram for explaining an overall example of machine learning performed according to a first embodiment;

FIG. 2 is a diagram for explaining an example of learning data;

FIG. 7 is a diagram illustrating an example of information stored in an attendance record data database (DB);

FIG. 8 is a diagram for explaining an example of determining the period of medical treatment using the attendance record data;

FIG. 16 is a diagram for explaining an exemplary hardware configuration.

DESCRIPTION OF EMBODIMENTS

Figure 3:
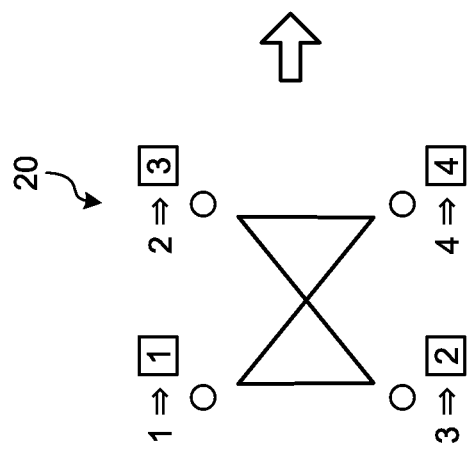
FIG. 3 is a diagram illustrating an exemplary relationship between a graph structure and tensors.

Preferred embodiments will be explained with reference to accompanying drawings. However, the invention is not limited by the embodiments described below. Moreover, the embodiments can be appropriately combined without causing any contradiction.

[a] First Embodiment

Overall Example

In recent years, the physical condition management of employees is ranked as an important task that is taken up by a business enterprise. In that regard, from the attendance record data of the employees, mental disorders that are likely to occur a few months ahead are predicted and measures such as counselling are taken at an early stage. Generally, full-time staff is employed for inspecting the attendance record data of an enormous number of employees, and for visually looking out for employees corresponding to characteristic work patterns such as frequent business trips, long hours of overtime work, continuous absence from work, absence without permission, or any combination of such phenomena. Regarding such characteristic work patterns, each full-time staff member may have a different standard, thereby making it difficult to clearly define the characteristic work patterns.

In that regard, in a first embodiment, as an example of deep learning using the deep tensor, the explanation is given about an example in which the attendance record data of employees is treated as the target for learning; and the attendance record data of the persons having a poor health condition and the attendance record data of the persons having a normal health condition are input to the deep tensor, and a prediction model meant for predicting mental disorders of employees is learnt. FIG. 1 is a diagram for explaining an overall example of machine learning performed according to the first embodiment. As illustrated in FIG. 1, a learning device 100 according to the first embodiment is an example of a computer device that generates a prediction model by performing machine learning of attendance record data of employees that contains the daily attendance at work, the clock-out time, the use of leaves, and the business trips; and that makes use of the post-learning prediction model and, by referring to the attendance record data of a target employee for prediction, predicts whether or not that employee will take medical treatment (take leave of absence). Herein, the explanation is given for an example in which the same learning device 100 performs a learning operation and a prediction operation. Alternatively, the two operations can be performed in different devices.

More particularly, the learning device 100 treats, as learning data, the attendance record data (label=medical treatment) of the persons who have a poor health condition and who have taken medical treatment in the past as well as the attendance record data (label=no medical treatment) of the persons who have a normal health condition and who have not taken medical treatment in the past; and generates a prediction model using the deep tensor that performs deep learning (DL) of data having a graph structure. Then, using the prediction model in which the learning result is applied, the learning device 100 estimates the correct event (label of data having a new graph structure).

For example, for each target, the learning device 100 generates a tensor including a plurality of elements that multi-dimensionally represent the features of the target over a period of time set in advance. When the target satisfies conditions set in advance, the learning device 100 identifies the period of time corresponding to the conditions in the target learning data for tensorization. Then, the learning device 100 generates a tensor in which the period of time after the concerned period of time has a lighter weight than the weight of the period of time before the concerned period of time; performs tensorial decomposition of the generated tensor; and performs deep-tensor-based learning.

The following explanation is given about the learning data that is input to the deep tensor. FIG. 2 is a diagram for explaining an example of the learning data. The learning data contains attendance record data taken for every six months and contains a label indicating whether or not there is any record of taking medical treatment within three months after the six months. In FIG. 2(a) is illustrated the attendance record data that is of a person having a poor health condition and that is labeled as "(medical treatment)". In FIG. 2(b) is illustrated the attendance record data that is of a person having a normal health condition and that is labeled as "(no medical treatment)" indicating no previous medical treatment. As illustrated in FIG. 2, the learning device 100 according to the first embodiment learns the prediction model with "attendance record data for six months, label (medical treatment)" and "attendance record data for six months, label (no medical treatment)" serving as the learning data. After performing the learning, from the attendance record data of a particular person for six months, the learning device 100 predicts whether or not that person will take medical treatment within the next three months. Meanwhile, the hatched portions in FIG. 2 indicate the periods in which leave of absence was taken.

Given below is the explanation about the deep tensor. The deep tensor represents deep learning in which a tensor (graph information) is used as the input and in which learning of a neural network is performed along with automatically extracting a partial graph structure that would contribute in the determination. The extraction operation is performed by learning the neural network along with learning the parameters of tensorial decomposition of the input tensor data.

Figure 4:
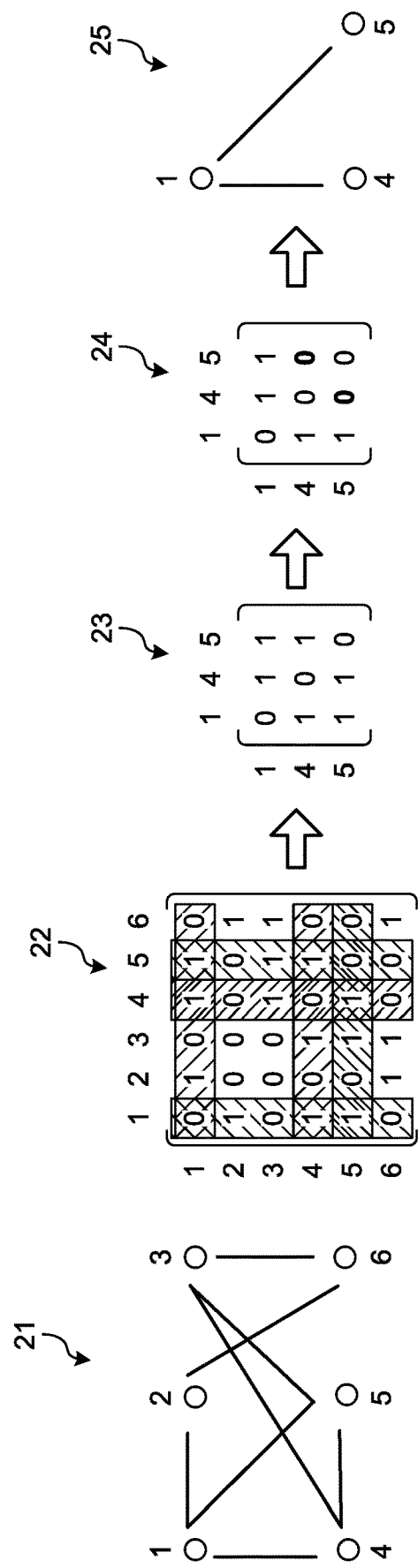
FIG. 4 is a diagram illustrating an example of extraction of a partial graph structure.

Given below with reference to FIGS. 3 and 4 is the explanation about a graph structure. FIG. 3 is a diagram illustrating an exemplary relationship between a graph structure and tensors. In a graph 20 illustrated in FIG. 3, four nodes are joined by edges indicating the relationship among the nodes (for example, "the coefficient of correlation is equal to or greater than a predetermined value"). The nodes that are not joined by edges do not have that relationship therebetween. In the case of expressing the graph 20 as second rank tensors, that is, as matrices; for example, the matrix based on the left-side numbers of the nodes is expressed as a "matrix A", and the matrix based on the right-side numbers of the nodes (the numbers enclosed in enclosures) is expressed as a "matrix B". Regarding the elements of these matrices; "1" is written when the corresponding nodes are joined (connected), and "0" is written when the corresponding nodes are not joined (not connected). In the following explanation, such matrices are called incidence matrices. Herein, the "matrix B" can be generated by simultaneously substituting the second and third rows and the second and third columns of the "matrix A". In the deep tensor, by performing such substitution, the processing is performed by ignoring the differences in order. That is, in the deep tensor, the "matrix A" and the "matrix B" are ignored as far as the order is concerned and are treated as the same graph. Regarding the tensors having the ranks equal to or higher than the third rank, the same processing is performed.

FIG. 4 is a diagram illustrating an example of extraction of a partial graph structure. In a graph 21 illustrated in FIG. 4, six nodes are joined by edges. When expressed as a matrix (tensor), the graph 21 can be expressed as a matrix 22. Then, a partial graph structure can be extracted as a result of performing the following operations in combination with respect to the matrix 22: an operation of interchanging particular rows and columns, an operation of extracting particular rows and columns, and an operation of substituting "0" for non-zero elements in an incidence matrix. For example, when a matrix corresponding to nodes 1, 4, and 5 of the matrix 22 is extracted, a matrix 23 is obtained.

Subsequently, when the values between the nodes 4 and 5 of the matrix 23 are substituted with "0", a matrix 24 is obtained. Then, as the partial graph structure corresponding to the matrix 24, a graph 25 is obtained.

Such an extraction operation for extracting a partial graph structure is implemented by performing a mathematical operation called tensor decomposition. In the tensor decomposition, an n-th rank tensor that is input is approximated using the product of tensors having the ranks equal to or lower than the n-th rank. For example, an n-th rank tensor that is input is approximated using the product of a single n-th rank tensor (called a core tensor) and n number of tensors having lower ranks (when n>2 holds true, usually a second rank tensor is used, that is, a matrix is used). However, such decomposition is not unique, and an arbitrary partial graph structure in the graph structure represented by the input data can be included in the core tensor.

Figure 5:
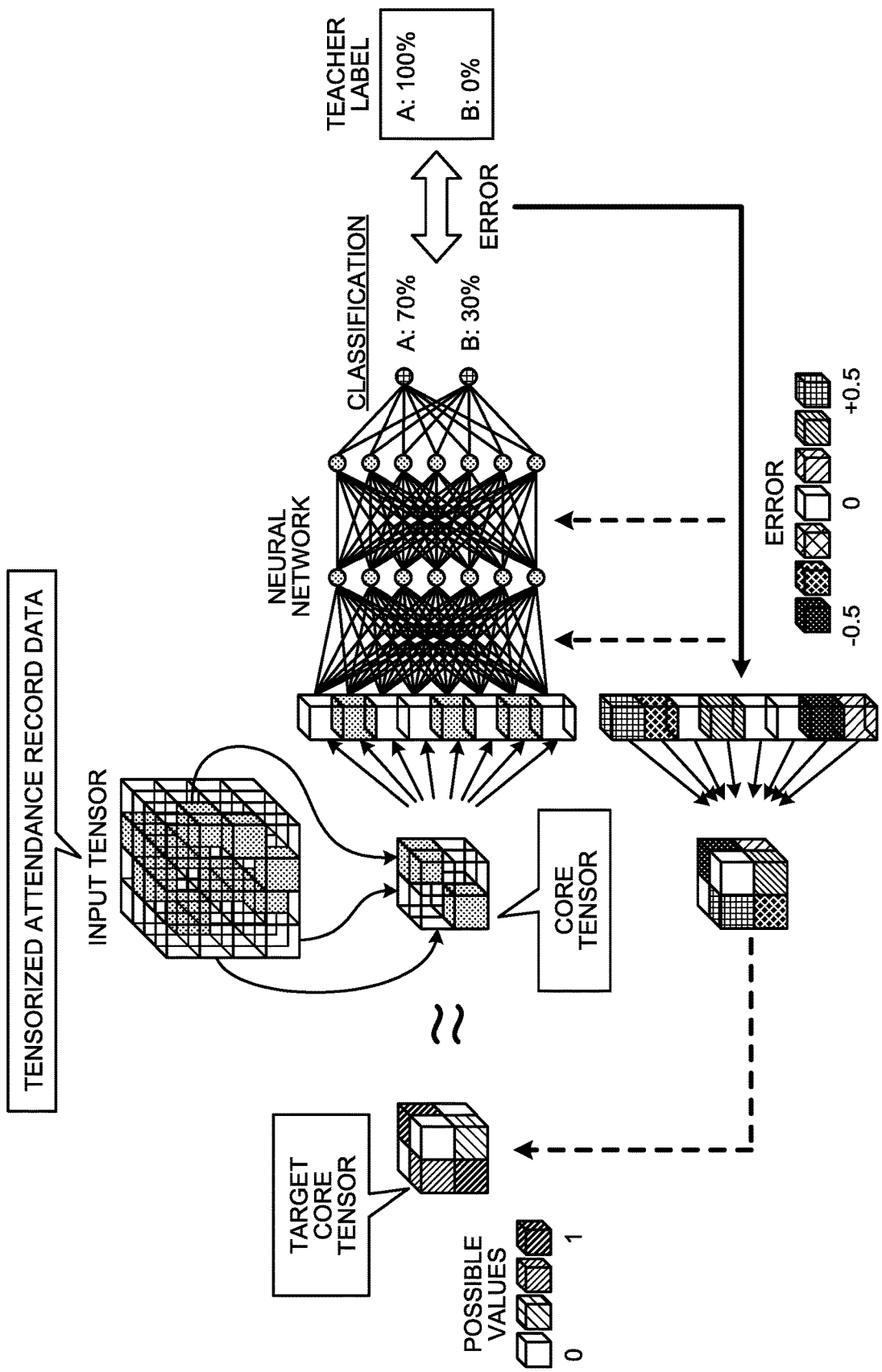
FIG. 5 is a diagram for explaining an example of learning deep tensor.

Given below is the explanation about the learning of the deep tensor. FIG. 5 is a diagram for explaining an example of learning the deep tensor. As illustrated in FIG. 5, the learning device 100 generates an input tensor from attendance record data having a teacher label (label A) such as "medical treatment". Then, the learning device 100 performs tensor decomposition of the input tensor, and generates a core tensor that is similar to a target core tensor that was initially generated in a random manner. Subsequently, the learning device 100 inputs the core tensor to a neural network (NN) and obtains the classification result (label A: 70%, label B: 30%). Then, the learning device 100 calculates the classification error between the classification result (label A: 70%, label B: 30%) and teacher labels (label A: 100%, label B: 0%).

Herein, the learning device 100 implements an expanded error propagation method that represents the expansion of the error backpropagation method, and performs learning of the prediction model and learning of the method for tensor decomposition. That is, with respect to the input layer, the intermediate layers, and the output layer of the neural network; the learning device 100 enables propagation of the classification error to the lower layers, and corrects various parameters of the neural network in such a way that the classification error becomes smaller. Moreover, the learning device 100 enables propagation of the classification error up to the target core tensor, and corrects the target core tensor in such a way that the target core tensor approaches the partial structure of the graph contributing in prediction, that is, approaches either the characteristic pattern indicating the characteristics of the person having a poor health condition or the characteristic pattern indicating the characteristics of the person having a normal health condition.

Meanwhile, at the time of performing post-learning prediction, the prediction result can be obtained by converting the input tensor into the core tensor (a partial pattern of the input tensor) according to tensor decomposition and by inputting the core tensor to the neural network. In the tensor decomposition, the core tensor gets converted to become similar to the target core tensor.

Then, at the time of performing learning with the use of a tensor generated from the attendance record data of each person having a normal health condition and a tensor generated from the attendance record data of each person having a poor health condition, regardless of whether or not medical treatment is included in the period of time clipped as a single set of learning data (for example, (six months)+ (three months for label assignment)), the learning device 100 refers to the entire period of time of the attendance record data and identifies each person who has experienced taking medical treatment in the past (hereinafter, called "person with medical history"). Subsequently, when core-tensorization is performed (i.e., when a partial pattern is extracted), regarding each person with medical history who is likely to have data that is partially similar to a pattern of irregular attendance record serving as a sign of being in the stage prior to taking new medical treatment, the learning device 100 reduces the weight of the tensor corresponding to the data for the period of time after the end of medical treatment (after the resumption of normal work). As a result, even if the attendance record data of a person with medical history is partially similar to the attendance record data of a person who has a poor health condition and who intends to newly take medical treatment, as a result of reducing the weight of the data of the persons with medical history indicated by frequent leave of absence or frequent late arrival, the learning device 100 no more processes that data as the core tensor which is same as a sign of being in the stage prior to taking new medical treatment. Hence, it becomes possible to hold down the deterioration in the accuracy of predicting new medical treatment.

Functional Configuration

Figure 6:
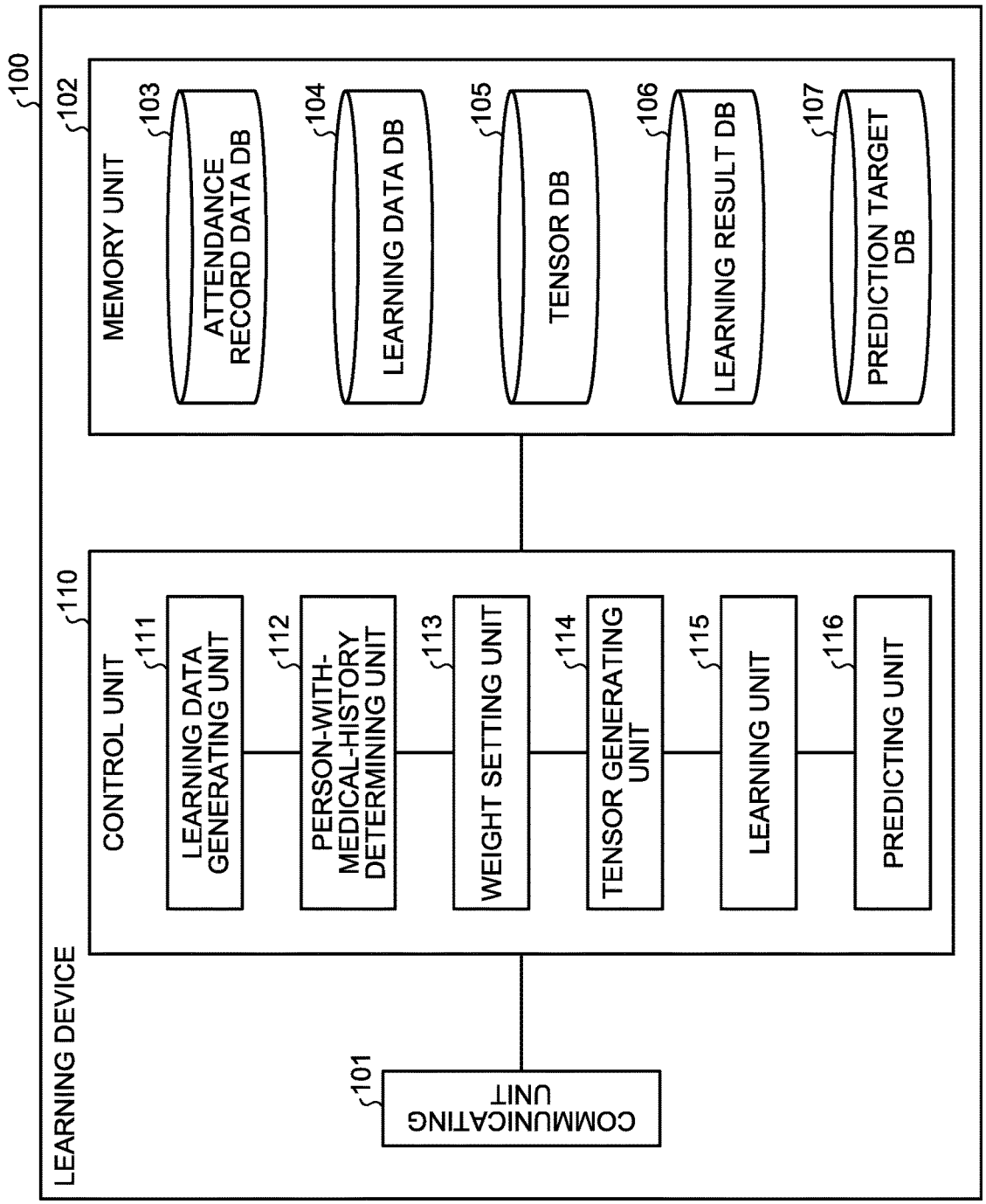
FIG. 6 is a functional block diagram illustrating a functional configuration of a learning device according to the first embodiment.

FIG. 6 is a functional block diagram illustrating a functional configuration of the learning device 100 according to the first embodiment. As illustrated in FIG. 6, the learning device 100 includes a communicating unit 101, a memory unit 102, and a control unit 110.

The communicating unit 101 is a processing unit for controlling the communication with other devices and, for example, represents a communication interface. For example, from an administrator terminal, the communicating unit 101 receives a processing start instruction, learning data, and an input tensor that is obtained by tensorization of learning data. Moreover, the communicating unit 101 outputs the learning result and the post-learning prediction result to the administrator terminal.

The memory unit 102 is an example of a memory device used to store computer programs and data and, for example, represents a memory or a hard disk. Herein, the memory unit 102 is used to store an attendance record data database (DB) 103, a learning data DB 104, a tensor DB 105, a learning result DB 106, and a prediction target DB 107.

The attendance record data DB 103 is a database for storing the attendance record data related to the attendance of the employees. The stored attendance record data is obtained from the attendance records kept in business enterprises, and can be obtained from various known attendance management systems. FIG. 7 is a diagram illustrating an example of information stored in the attendance record data DB 103. As illustrated in FIG. 7, in the attendance record data, the following items are stored in a corresponding manner: employee number, date, day, attendance-absence category, clock-in time, clock-out time, overtime hours, and business trip. Herein, the attendance-absence category item includes categories such as attendance, medical treatment, and leave of absence.

In the example illustrated in FIG. 7, the attendance record data of the employee having an employee number "100" is illustrated. For example, the second row in FIG. 7 represents the attendance record data for "Apr. 2, 2015 Thursday"; and it is indicated that, on that day, the concerned employee did not have any business trip, arrived at work at "8:49", left for the day at "0:00", and did overtime work for the overtime hours of "360 minutes". Similarly, the seventh row in FIG. 7 represents the attendance record data for "Aug. 24, 2015 Wednesday"; and it is indicated that the concerned employee went off for medical treatment from that Wednesday till "Oct. 4, 2015 Tuesday". Meanwhile, the attendance record data need not be in the units of days, and can be in the units of weeks or months.

The learning data DB 104 is a database for storing the target learning data for tensorization. More particularly, the learning data DB 104 is used store sets of learning data each of which contains data obtained by clipping the attendance record data for a period of six months and contains a label. For example, the learning data DB 104 is used to store "learning data a, label (no medical treatment)" and "learning data b, label (medical treatment)" as sets of "data, label".

For example, the attendance record data for every six months is treated as a single set of learning data. Then, if a medical treatment period is included within the next three months, then "medical treatment" is set as the label. However, if no medical treatment period is included within the next three months, then "no medical treatment" is set as the label. Meanwhile, if a period of medical treatment is included in the attendance record data for six months, then that data is not used as the learning data. That is because, regarding a person who already has "medical treatment" recorded in the attendance record data for six months that represents the source data for prediction (the input for prediction), it is clear that the person has been recently taking medical treatment and is not considered as the target for medical treatment prediction in the next three months.

The tensor DB 105 is a database for storing a tensor (tensor data) generated from the learning data of each employee. Thus, the tensor DB 105 is used to store tensor data in which tensors and labels are held in a corresponding manner. For example, the tensor DB 105 is used to store "tensor number 1, label (no medical treatment)" and "tensor number 2, label (medical treatment)" as sets of "data number, label". Meanwhile, each stored tensor can be generated in a different device other than the learning device 100, or can be generated in the learning device 100.

The learning result DB 106 is a database for storing the learning result. For example, the learning result DB 106 is used to store the determination result (the classification result) obtained regarding the learning data by the control unit 110, and to store various parameters of the neural network and various parameters of the deep tensor as learnt using machine learning and deep learning.

The prediction target DB 107 is a database for storing the attendance record data for which the presence or absence of new medical treatment is to be predicted using the learnt prediction model. For example, the prediction target DB 107 is used to store the target attendance record data for prediction or to store the tensors generated from the target attendance record data for prediction.

The control unit 110 is a processing unit that controls the entire learning device 100 and, for example, represents a processor. The control unit 110 includes a learning data generating unit 111, a person-with-medical-history determining unit 112, a weight setting unit 113, a tensor generating unit 114, a learning unit 115, and a predicting unit 116. The learning data generating unit 111, the person-with-medical-history determining unit 112, the weight setting unit 113, the tensor generating unit 114, the learning unit 115, and the predicting unit 116 represent examples of electronic circuits included in the processor or represent examples of processes executed by processor.

The learning data generating unit 111 is a processing unit that, from the various sets of attendance record data stored in the attendance record data DB 103, generates learning data made of pairs of data for predetermined periods of time having different start timings and labels corresponding to the start timings. More particularly, the learning data generating unit 111 allows duplication from the attendance record data of a single person, and samples the data for the specified period of time. Moreover, the learning data generating unit 111 extracts, from each set of attendance record data, a plurality of sets of data having different starts to the period of time (different start timings); and, regarding each set of data, either sets the label "medical treatment" if a period of medical treatment is included within three months from the end timing of the data or sets the label "no medical treatment" if no period of medical treatment is included within three months from the end timing of the data.

For example, from the attendance record data from January to December, the learning data generating unit 111 extracts the attendance record data from January to June. If no period of medical treatment is included within the three months from July to September, then the learning data generating unit 111 attaches the label "no medical treatment" to the extracted attendance record data and generates learning data. Subsequently, from the attendance record data from January to December, the learning data generating unit 111 extracts the attendance record data from February to July. If a period of medical treatment is included within the three months from August to October, then the learning data generating unit 111 attaches the label "medical treatment" to the extracted attendance record data and generates learning data.

The person-with-medical-history determining unit 112 is a processing unit that, based on the attendance record data serving as the basis of each set of learning data, determines whether or not the concerned employee is a person with medical history. For example, instead of clipping the attendance record data for a period of six months as used in prediction, the person-with-medical-history determining unit 112 refers to the attendance record data representing the entire data section of the concerned employee, and determines that the person is a person with medical history if a period of medical treatment is included or determines that the person is a person with a normal health condition if no period of medical treatment is included. Then, the person-with-medical-history determining unit 112 notifies the weight setting unit about the determination result regarding each set of learning data.

Meanwhile, a person with medical history is not limited to an employee who has had a period of medical treatment within the period of time used as a single set of learning data, but implies an employee who has had a period of medical treatment across the entire attendance record data in the past. For example, when the period of medical treatment is two years before the time of learning, if the data for only the most recent six months is referred to, sometimes the concerned person is not a person having a poor health condition but represents a person with medical history.

The weight setting unit 113 is a processing unit that determines whether or not each set of learning data corresponds to the period of time starting after the end of medical treatment of the concerned person with medical history, and sets the weight according to the determination result. That is, regarding the learning data of a person with medical history that represents an example of a particular condition, the weight setting unit 113 sets the weight in such a way that the degree of importance is lowered for the data corresponding to the resumption of normal work after the end of medical treatment. For example, regarding each set of learning data generated from the attendance record data from which it was determined by the person-with-medical-history determining unit 112 that the concerned person is a person with medical history, if the learning data corresponds to the data for the period of time starting after the resumption of normal work once the period of medical treatment is over, the weight setting unit 113 lowers the weight regarding that particular learning data.

Explained below with reference to FIG. 8 is the setting performed regarding the period of medical treatment and the weight. FIG. 8 is a diagram for explaining an example of determining the period of medical treatment using the attendance record data. As illustrated in FIG. 8, at the time of tensorization, the weight setting unit 113 determines whether each set of learning data is before or after the "period of medical treatment". If the "period of medical treatment" is from "Aug. 24, 2016" to "Oct. 4, 2016", then the weight setting unit 113 sets the weight "1" for the learning data corresponding to the time before "Aug. 24, 2016" representing the start of medical treatment, and sets the weight "0" for the learning data corresponding to the time after "Oct. 4, 2016" representing the end of medical treatment.

That is, the pre-medical-treatment period of time that is before the period of medical treatment is determined to be important for extraction as the core tensor that represents the partial pattern constituting a factor for taking medical treatment (i.e., the partial pattern affecting the prediction), and hence the weight "1" is set. On the other hand, the post-medical-treatment period of time that is after the period of medical treatment is determined not to be important for extraction as the core tensor that represents the partial pattern constituting a factor for taking medical treatment, and hence the weight "0" is set.

The tensor generating unit 114 is a processing unit for tensorization of the sets of learning data. More particularly, regarding each set of learning data which is stored in the learning data DB 104 and for which the weight setting unit 113 has set the weight, the tensor generating unit 114 generates a tensor configured with the elements included in the learning data and stores the tensor in the tensor DB 105. Herein, regarding each set of learning data which is stored in the learning data DB 104 and for which the weight setting unit 113 has set the weight, the tensor generating unit 114 generates, for example, a fourth rank tensor that is configured with four elements included in the learning data and stores the tensor in the tensor DB 105. Moreover, the tensor generating unit 114 stores the label (medical treatment) or the label (no medical treatment), which is to be attached to the learning data, in a corresponding manner to the tensor.

More particularly, the tensor generating unit 114 and generates a tensor from the learning data while treating, as dimensions, the attributes that are assumed to characterize the inclination to take medical treatment. For example, the tensor generating unit 114 generates a four-dimensional fourth rank tensor having the following four elements: month, date, attendance-absence category, and presence or absence of business trips. Meanwhile, when the data for six months is available, the count of the "month" element is six; the count of the "date" element is "31" because the maximum number of days in a month is 31; the count of the "attendance-absence category" element is three if attendance, leave, and holiday represent the attendance-absence categories; and the count of the element "presence or absence of business trips" is two because either a business trip is undertaken or not. Thus, the tensor that is generated from the learning data becomes a "6×31×3×2" tensor in which the elements of the learning data that correspond to the attendance-absence category and the presence or absence of business trips each month and on in each date are set to "1" and the other elements are set to "0".

Figure 9:
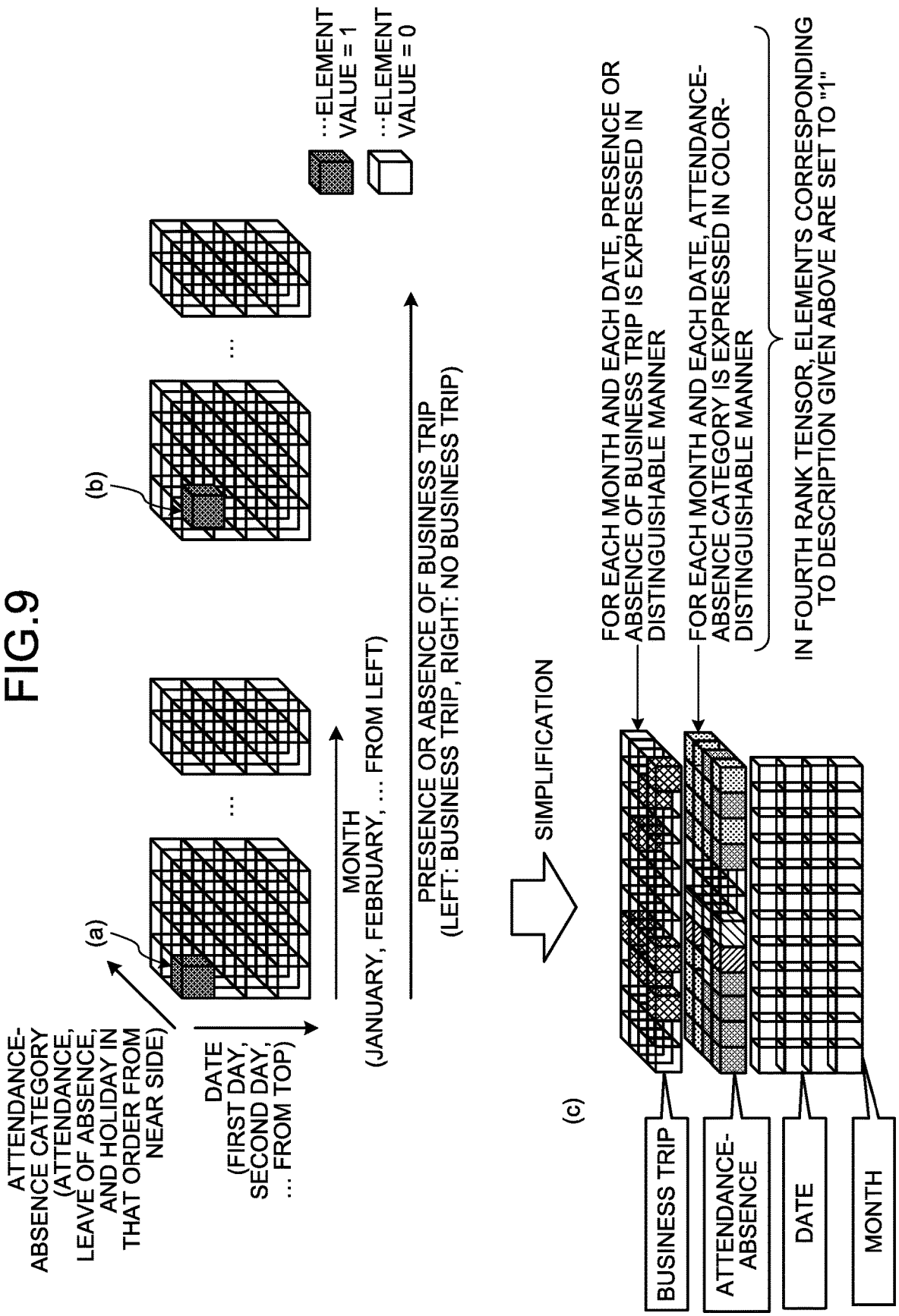
FIG. 9 is a diagram for explaining the tensorization.

FIG. 9 is a diagram for explaining the tensorization. As illustrated in FIG. 9, a tensor that is generated by the tensor generating unit 114 represents data indicating "month" in the horizontal direction, indicating "date" in the vertical direction, indicating "attendance-absence category" in the depth direction, indicating "business trip" on the left-hand side, and indicating "no business trip" on the right-hand side. Herein, the dates are written in ascending order from top. The attendance-absence categories include attendance, leave of absence, and holiday written in that order starting from the near side. For example, in FIG. 9(*a*) are illustrated the elements indicating that a person arrived at work on the first day of the first month and went for a business trip; and in FIG. 9(*b*) are illustrated the elements indicating that a person took a leave of absence on the second day of the first month and did not go for any business trip.

Meanwhile, in the first embodiment, the abovementioned tensor is simplified and illustrated in FIG. 9(*c*). That is, the tensor is expressed in a cube-like shape in which the four elements of "month", "date", "attendance-absence category", and "presence or absence of business trips" are illustrated in an overlapping manner. Herein, the business trips in each month and on each date are expressed in a distinguishing manner, and the attendance-absence category on each date of each month is expressed in a distinguishing manner.

Meanwhile, at the time of performing prediction, the tensor generating unit 114 implements an identical method to the method implemented at the time of performing learning; and, from the attendance record data of each prediction target as stored in the prediction target DB 107, generates the tensor to be input to the neural network.

The learning unit 115 is a processing unit that receives input of the tensors and the labels generated from the sets of learning data, and accordingly learns the prediction model using the deep tensor and learns the method of tensor decomposition. More particularly, the learning unit 115 performs learning using the property of the deep tensor that "a partial structure of a graph (tensor) is recognizable". For example, in an identical manner to the method explained with reference to FIG. 5, the learning unit 115 extracts the core tensor from the target tensor for input (input tensor) and inputs the core tensor to the neural network; and calculates the error (classification error) between the classification result obtained from the neural network and the label attached to the input tensor. Then, using the classification error, the learning unit 115 learns the parameters of the neural network and optimizes the target core tensor. Subsequently, once the learning is over, the learning unit 115 stores various parameters as the learning result in the learning result DB 106.

Figure 10:
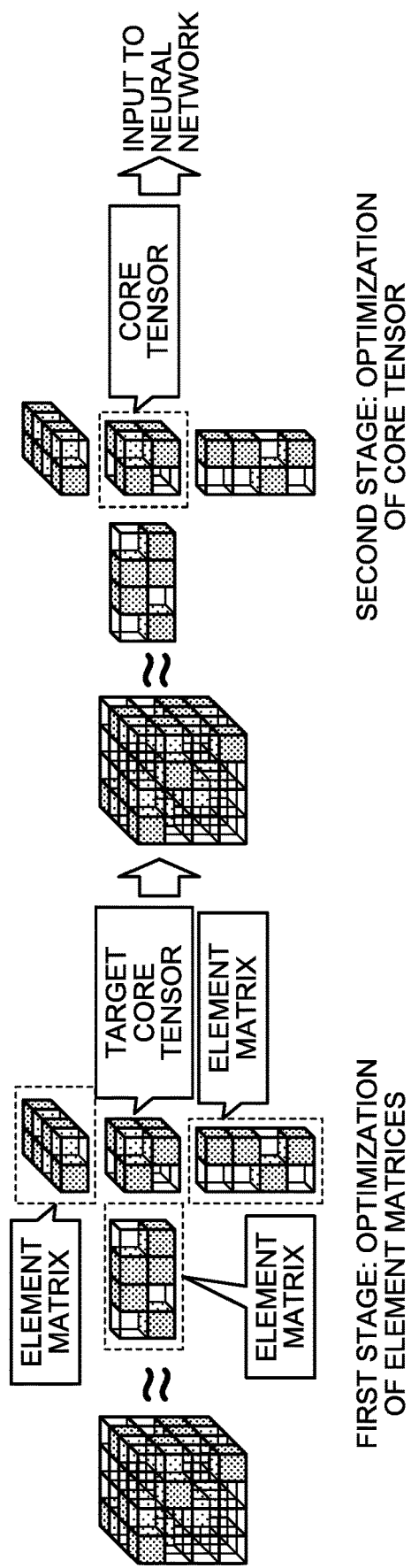
FIG. 10 is a diagram for explaining an input tensor having the weight "1" set therein regarding a person with a normal health condition.
Figure 11:
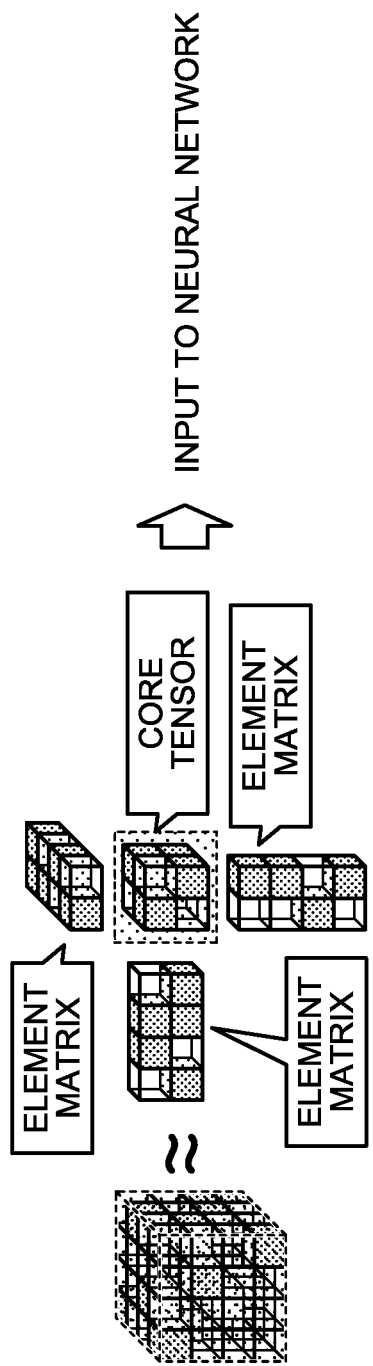
FIG. 11 is a diagram for explaining an input tensor having the weight "0" set therein regarding a person with medical history.

The following explanation is given about input tensors for which the weight is set. FIG. 10 is a diagram for explaining an input tensor having the weight "1" set therein regarding a person with a normal health condition. FIG. 11 is a diagram for explaining an input tensor having the weight "0" set therein regarding a person with medical history. Since a tensor represents a linear quantity, weighting a tensor implies varying the length of the tensor by multiplying a numerical value between zero and one to the original length or multiplying a higher numerical value to the original length.

In the tensor decomposition explained in the first embodiment, the core tensor is calculated to be similar to the target core tensor, and the structure that is important in classification is placed at the position similar to the core tensor. Then, the neural network is learnt using the core tensor, so that classification of a high degree of accuracy is achieved. The tensor decomposition is calculated by performing optimization in two stages. As illustrated in FIG. 10, in the first stage, using the target core tensor that is provided, only the element matrices are optimized in such a way that the input tensor is approximated in the most appropriate manner. In the second stage, using the element matrices optimized in the first stage, the core tensor is optimized in such a way that the input tensor is approximated in the most appropriate manner.

Meanwhile, weighting an input tensor implies numerical weighting of the core tensor (i.e., varying the linear quantity). As illustrated in FIG. 11, if all input tensors are weighted by "0", the core tensor also gets weighted by "0", and all data of the persons with medical history gets input to the neural network with the core tensor weighted by "0". Hence, even if the pre-weighting input tensors are identical tensors, the tensors weighted by "1" and the tensors weighted by "0" are learnt as different inputs, so that the irregular attendance situation of a person occurring before newly taking medical treatment and the irregular attendance situation of a person with medical history can be appropriately learnt as different situations.

The more detailed explanation is as follows. Regarding the persons with medical history, all data is input as the weighted core tensor to the neural network, and is classified by getting output from the neural network. Then, the classification result is compared with the teacher labels, and the parameters of the neural network are updated in such a way that the error is oppositely propagated and is minimized. At that time, since the error information of each element is obtained in return due to backpropagation, the target core tensor too is updated based on that error information. Then, in order to achieve similarity with the updated target core tensor, a new core tensor is generated by taking out elements from the weighted input tensors. Then, the new core tensor is input to the neural network, and is classified by getting output from the neural network. Subsequently, the classification result is compared with the teacher labels, and the parameters of the neural network are updated in such a way that the error is oppositely propagated and is minimized. At that time, since the error information of each element is obtained in return due to backpropagation, the target core tensor too is updated based on that error information. Thus, the learning is repeatedly performed until the error between the classification result and the teacher labels is minimized. As a result, the optimized target core tensor and the optimized parameters of the neural network get decided.

The predicting unit 116 is a processing unit that makes use of the learning result and predicts the label of the target data for determination. More particularly, the predicting unit 116 reads various parameters from the learning result DB 106, and builds a neural network in which the various parameters are set. Then, the predicting unit 116 inputs a tensor, which is generated from the target attendance record data for prediction, to the neural network. Subsequently, the predicting unit 116 outputs the prediction result regarding whether or not medical treatment would be taken. Then, the predicting unit 116 displays the prediction result in a display or sends the prediction result to the administrator terminal.

Moreover, the predicting unit 116 refers to the attendance record data of the target employee for prediction; determines whether or not a period of medical treatment is included before the target attendance record data for prediction; and performs prediction if the concerned employee is a person with a normal health condition on account of non-inclusion of a period of medical treatment, or outputs a warning if the concerned employee is a person with medical history on account of inclusion of a period of medical treatment.

Flow of Learning Operation

Figure 12:
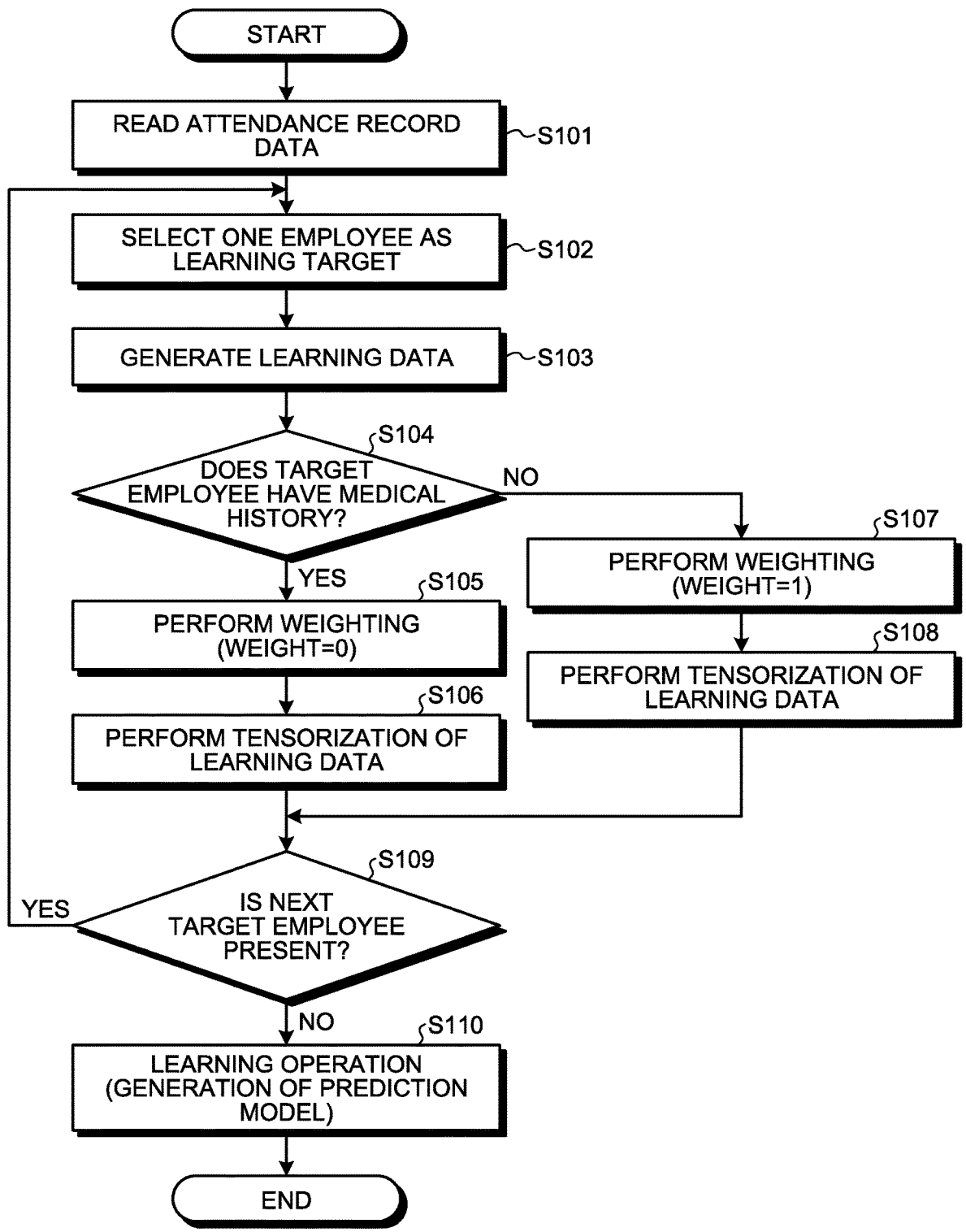
FIG. 12 is a flowchart for explaining a flow of operations performed at the time of learning.

FIG. 12 is a flowchart for explaining a flow of the operations performed at the time of learning. As illustrated in FIG. 12, the learning data generating unit 111 reads the attendance record data from the attendance record data DB 103 (S101), and selects a single employee as the learning target (S102).

Then, the learning data generating unit 111 clips the data for six months from the attendance record data; attaches a label to the clipped data depending on whether or not a period of medical treatment is included in the attendance record data for the next three months; and generates learning data (S103). Herein, if medical treatment is included in the clipped data for six months, then that data is not considered as the learning data.

Subsequently, the operations from S104 to S108 are performed for each set of learning data. More particularly, the person-with-medical-history determining unit 112 refers to the attendance record data of the target employee and determines whether or not the target employee is a person with medical history (S104).

If the target employee is a person with medical history (Yes at S104), then the weight setting unit 113 assigns the learning data with the weight ("0") regarding the period of time that is after the end of medical treatment of the concerned employee (S105); and the tensor generating unit 114 performs tensorization of the weighted learning data (S106).

On the other hand, if the target employee is not a person with medical history (No at S104), then the weight setting unit 113 assigns the learning data with the weight ("1") (S107); and the tensor generating unit 114 performs tensorization of the weighted learning data (S108). That is, the weight remains unchanged.

Subsequently, if another target employee is present (Yes at S109), then the operations from S102 are performed again. When no more target employee is present (No at S109), then the learning unit 115 performs the learning operation (S110).

Flow of Prediction Operation

Figure 13:
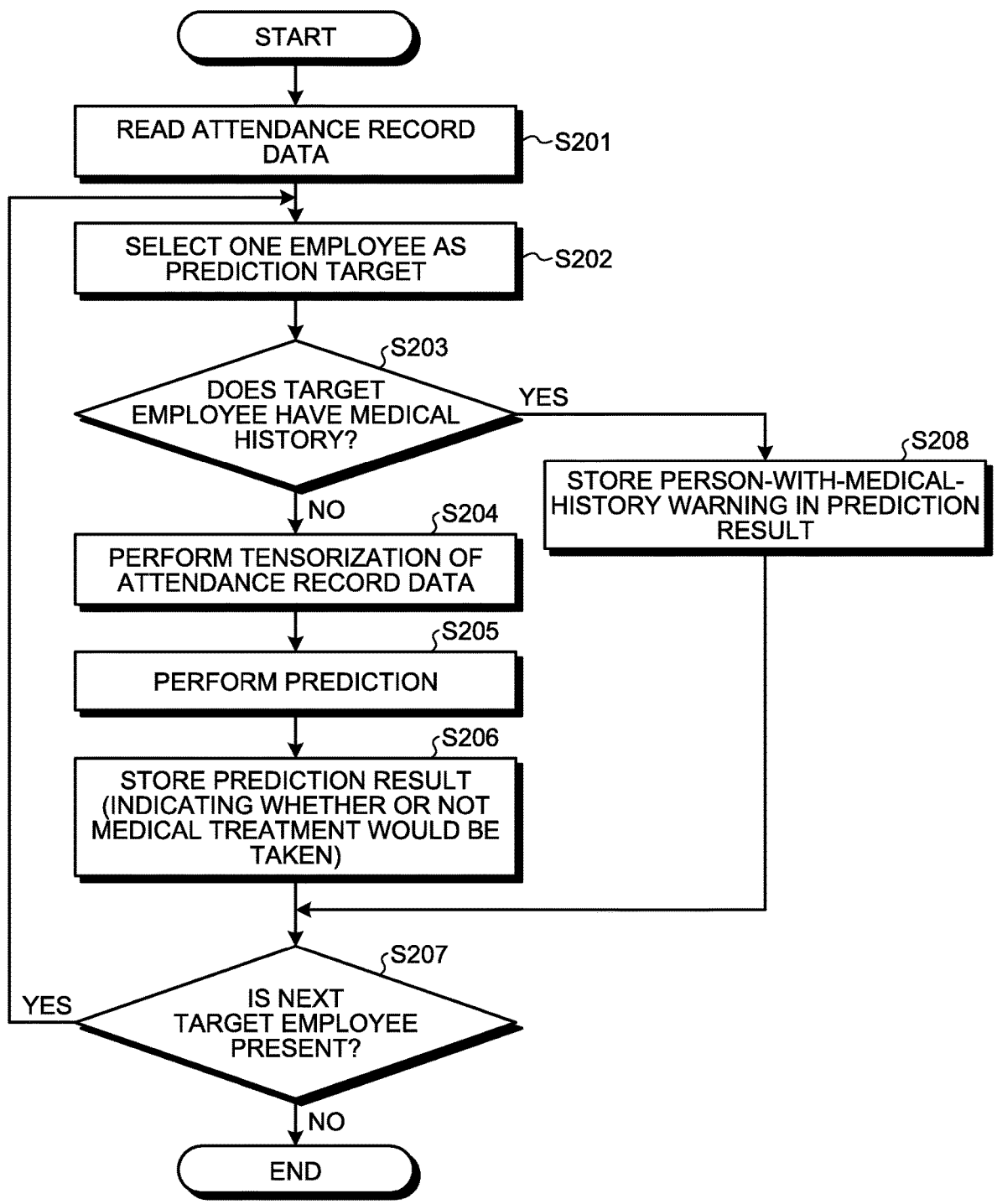
FIG. 13 is a flowchart for explaining a flow of operations performed at the time of prediction.

FIG. 13 is a flowchart for explaining a flow of the operations performed at the time of prediction. In an identical manner to the case of performing learning, regarding the target attendance record data for prediction too, it is predicted whether or not medical treatment would be taken within the next three months. As illustrated in FIG. 13, the predicting unit 116 reads the attendance record data from the prediction target DB 107 (S201) and selects a single employee as the prediction target (S202).

Then, the predicting unit 116 refers to the attendance record data of the target employee and determines whether or not the target employee is a person with medical history (S203).

If the target employee is not a person with medical history (No at S203), then the predicting unit 116 performs tensorization of the attendance record data (S204); performs prediction using the already-learnt prediction model (S205); and stores, in the memory unit 102, a label of the prediction result indicating whether or not the target employee would take medical treatment within the next three months (S206).

Subsequently, if another target employee is present (Yes at S207), then the operations from S202 are performed again. When no more target employee is present (No at S207), it marks the end of the operations. Meanwhile, at S203, if it is determined that the target employee is a person with medical history (Yes at S203); then the predicting unit 116 stores, in the prediction result, a person-with-medical-history warning (S208). Herein, at S203, the target employee being a person with medical history not only implies that the attendance record data in the period of time before the target attendance record data for prediction (i.e., before the attendance record data for six months) includes medical treatment, but can also imply that the target attendance record data for prediction (i.e., the attendance record data for six months) includes medical treatment thereby making the concerned employee not eligible as the prediction target.

Effect

As described above, the learning device 100 can make use of the property of the deep tensor that "a partial structure of the graph contributing in prediction (i.e., a partial pattern of a tensor) is extractable as the core tensor", and can perform accurate prediction even with only a small volume of learning data. Particularly, as a result of changing the weight of the tensor data for the period of time that is after the end of medical treatment of a person with medical history; even if the irregular attendance situation of a person occurring before newly starting medical treatment and the irregular attendance situation of a person with medical history indicate partially same attendance patterns in the attendance record data, the two situations can be appropriately learnt as different situations. That enables achieving enhancement in the accuracy of predicting the persons who would newly take medical treatment.

Moreover, the full-time staff typically employed to perform physical condition management of the employees can view the result obtained by the learning device 100 by checking the prediction targets representing the persons with medical history, and can confirm whether the persons with medical history who are highly likely to again take medical treatment are targets for follow-up. Furthermore, the learning device 100 can make use of the result of checking the prediction targets representing the persons with medical history; detect the persons with medical history who are highly likely to again take medical treatment; and output a "person-with-medical-history warning".

Figure 14:
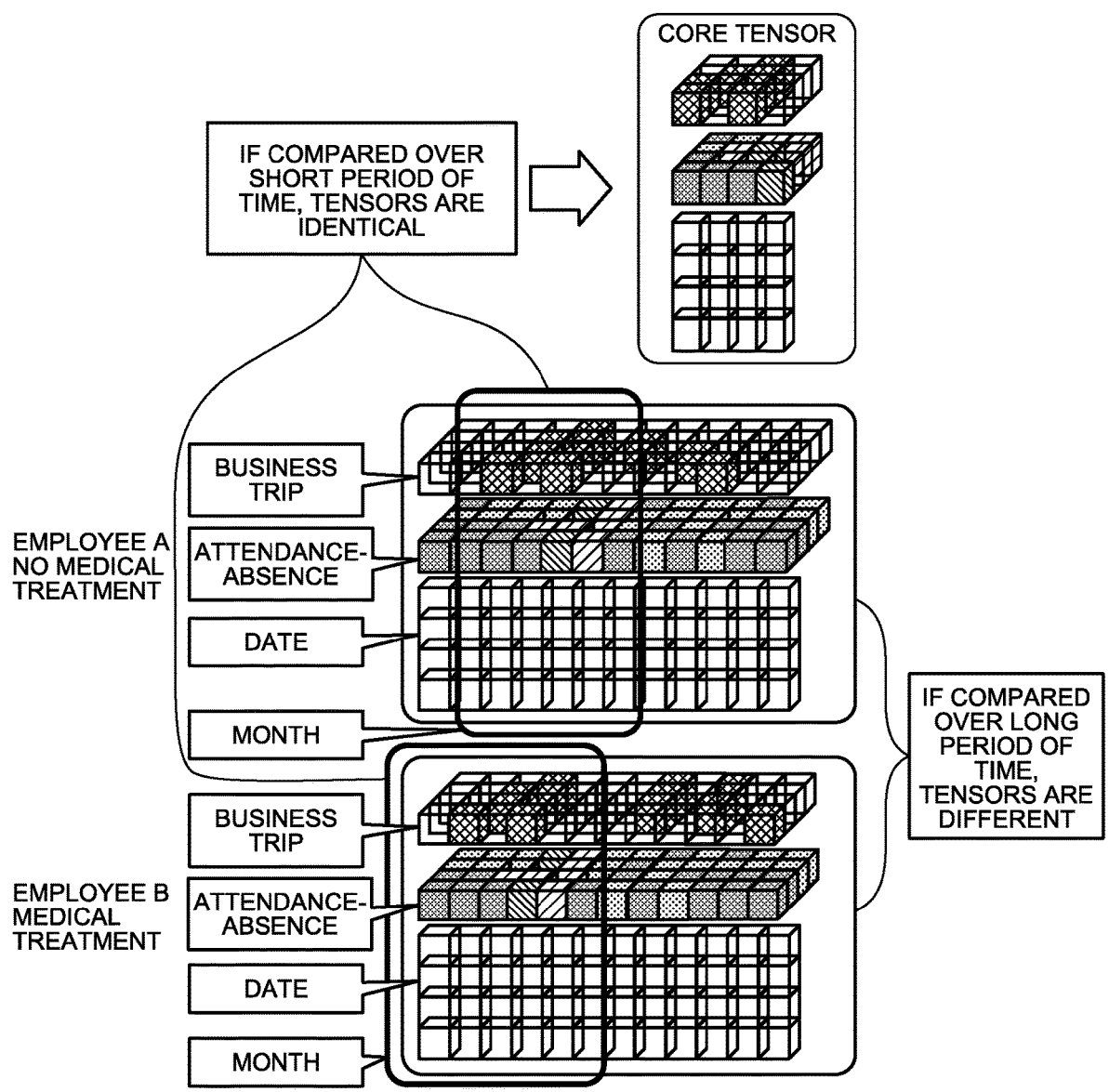
FIG. 14 is a diagram for explaining the issues faced in the standard tensorization.
Figure 15:
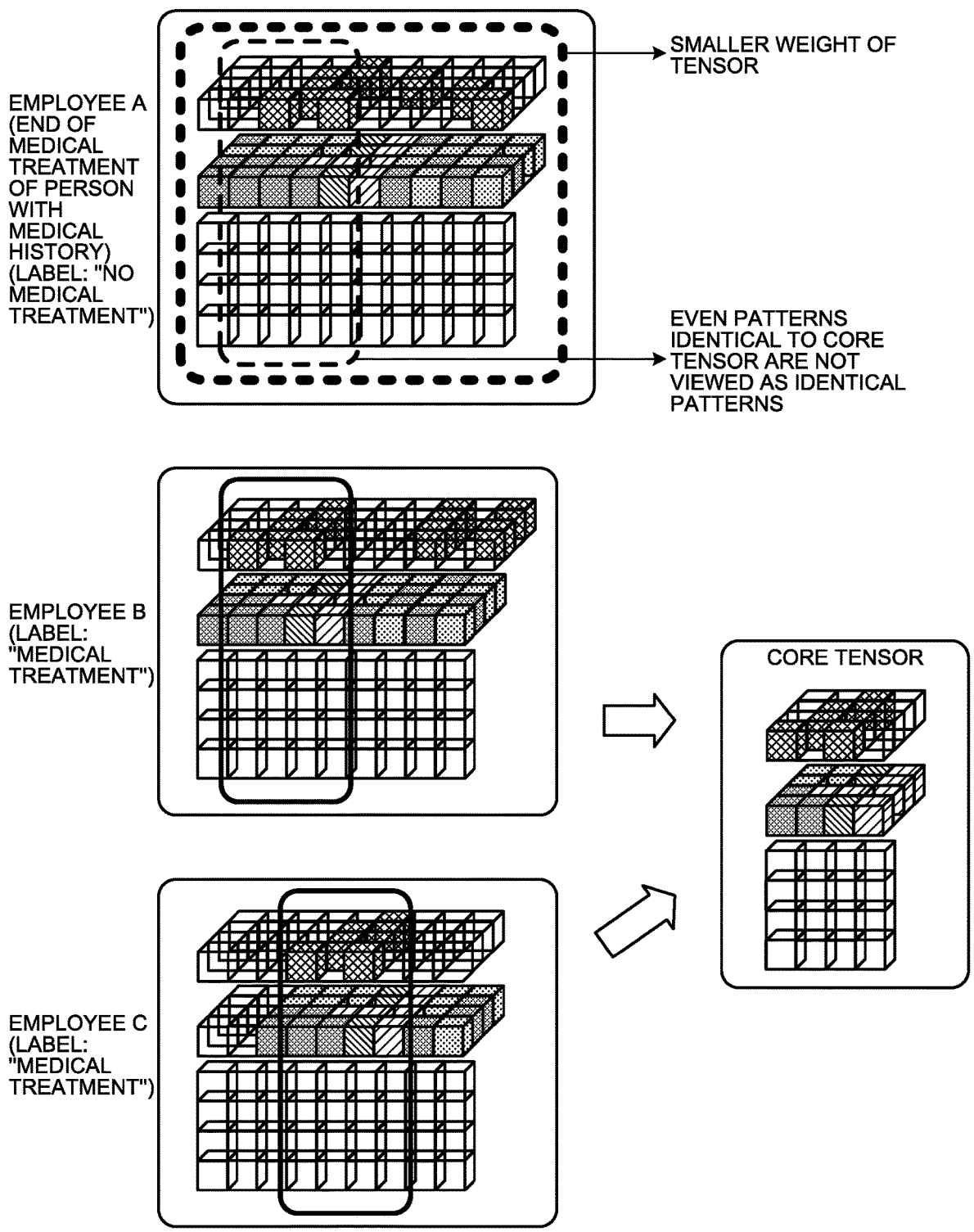
FIG. 15 is a diagram for explaining the effect of tensorization with weight attachment.

Given below is the explanation of a comparison example between the standard tensorization and the tensorization with weight attachment according to the first embodiment. FIG. 14 is a diagram for explaining the issues faced in the standard tensorization. FIG. 15 is a diagram for explaining the effect of tensorization with weight attachment. The following explanation is given about a comparison example between a tensor of the learning data of an employee A (label: no medical treatment), who is a person with medical history but has finished taking the medical treatment, and an employee B (label: medical treatment), who is a person planning to take medical treatment within three months.

As illustrated in FIG. 14, in the standard tensorization, although the tensor for the employee A and the tensor for the employee B are different tensors if compared over a long period of time, they are identical tensors if compared over only a short period of time. That is, there is a possibility that same core tensors get extracted. In that case, the two cases get processed as the same case examples. As a result, the data of the person with medical history becomes noise, thereby leading to deterioration in the accuracy of optimization of the target core tensor and learning of the neural network. Hence, there occurs deterioration in the accuracy of the prediction model.

In the first embodiment, as illustrated in FIG. 15, although the tensors for employees A, B, and C are different tensors if compared over a long period of time, they are identical tensors if compared over only a short period of time. That is, there is a possibility that a common pattern gets extracted as the core tensors. However, since the employee A is a person with medical history, the weight of the corresponding tensor is changed. Hence, even if the core tensor has the same pattern, it is not processed as the same pattern (core tensor) when input to the neural network, and is learnt as a separate case example. Meanwhile, the tensors for the employees B and C are learnt as a common pattern. As a result, it becomes possible to hold down the deterioration in the accuracy of the prediction model attributed to the learning data of the persons with medical history.

[b] Second Embodiment

Meanwhile, although the present invention has been described with reference to the embodiment described above, it is also possible to implement the invention in various forms other than the embodiment described above.

Learning

The learning operation described above can also be performed for an arbitrary number of times. For example, the learning operation can be performed using all sets of learning data, or can be performed only for a predetermined number of times. Moreover, regarding the method for calculating the classification error, a known calculation method such as the least square method can be implemented, or a standard calculation method used in neural networks can be implemented. Furthermore, the learning data and the attendance record data can be obtained from external devices.

Weight

In the embodiment, the explanation is given about an example in which "0" is set as the weight of a tensor that is after the end of medical treatment. However, that is not the only possible case. Alternatively, for example, it is possible to set a plurality of weights, such as the weight "1" for the period of time before taking medical treatment, the weight "0" for the period of one year after the end of medical treatment, and the weight (0.5) after that period of one year. Still alternatively, the weight "0" can be set to a tensor that is after the end of medical treatment, and the weight "0" can be reset to the original weight "1" after the elapse of two years after the end of medical treatment. Still alternatively, the target tensor for learning can be subjected to a change in the weight before and after the concerned period of time. For example, the weight of the period of time that is before the concerned period of time corresponding to predetermined conditions can be set to be greater than the weight of the period of time that is after the concerned period of time. Meanwhile, the numerical values of the weights are only exemplary, and it is possible to use any other values as long as the degree of importance of the data in the period of time before taking medical treatment can be set to a higher value and as long as the degree of importance of the data in the period of time after resumption of normal work can be set to a lower value. Moreover, depending on the predetermined conditions, the weight of the period of time that is before the concerned period of time corresponding to the predetermined conditions can be set to be smaller than the weight of the period of time that is after the concerned period of time.

Specified Conditions

In the first embodiment, the explanation is given for an example in which the tensor data of a person with medical history, who has experienced taking medical treatment, is subjected to a change in the weight. However, that is not the only possible case. For example, regarding a child-rearing employee or a caregiver employee who may have irregular work schedules not attributed to his or her own poor health condition, the data of that employee can become noise in the prediction of new medical treatment. Hence, the conditions for changing the weights of tensor data can be arbitrarily varied, such as treating the employees having irregular work schedules as the prediction targets.

In the embodiment described above, the explanation is given for an example in which, at the time of performing learning, the period of time of six months or three months is automatically extracted; a label such as "medical treatment" or "no medical treatment" is attached; and learning is performed. However, that is not the only possible case. Alternatively, for example, when the extraction of the period of time and the attachment of a label is performed in advance by the user, the provided data and the already-attached label can also be used. Moreover, the setting of a label is also only exemplary, and is not limited to "medical treatment" and "no medical treatment". Alternatively, it is possible to use various labels, such as "poor health condition" and "normal health condition" or "leave of absence" and "no leave of absence", that enable determination of the presence or absence of the persons having a poor health condition.

Meanwhile, although the attendance record data for six months is treated as the data to be used in prediction, that is not the only possible case. Alternatively, the period for the attendance record data can be arbitrarily changed such as to four months. Moreover, the explanation is given about the example in which the label is attached depending on whether or not medical treatment is taken within three months after the six months of the attendance record data. However, that is not the only possible case. Alternatively, for example, the period of time can be arbitrarily changed, such as to two months, after the six months of the attendance record data. Furthermore, in the embodiment described above, the explanation is given for an example in which the learning device 100 performs tensorization of the attendance record data. Alternatively, it is possible to obtain data that is tensorized by some other device, and then perform the operations described above.

Assumed System

In the embodiment described above, the explanation is given about an example in which the attendance record data is learnt and the employees who are likely to take medical treatment are predicted. However, that is not the only possible case. Alternatively, for example, the embodiment can be implemented for fault prediction using operation data of electronic components, or attack prediction using communication data, or congestion prediction using traffic data of roads.

Neural Network

In the present embodiment, it is possible to use various neural networks such as a recurrent neural network (RNN) or a convolutional neural network (CNN). Moreover, regarding the learning method, it is possible to implement various known methods besides the error backpropagation method. Meanwhile, a neural network has a multistage configuration including, for example, an input layer, intermediate layers (hidden layers), and an output layer; and each layer has the structure in which a plurality of nodes are joined by edges. Each layer has a function called an "activating function", and the edges have a "weight" assigned thereto. Thus, the value of each node is calculated from the value of the node in the previous layer, and the value of the weight of the edge joined thereto (a weight coefficient), and the activating function of the concerned layer. Regarding the calculation method, various known methods can be implemented.

Moreover, learning in a neural network implies correcting the parameters, that is, correcting the weight and the bias in such a way that the output layer has a correct value. In the error backpropagation method, a "loss function" is defined that indicates the extent of deviation of the value of the output layer from the correct state (the desired state); and the weight and the bias are updated using the method of steepest descent so that the loss function is minimized.

System

Process procedures, control procedures, specific names, and information including various kinds of data and parameters represented in the above description and drawings may be optionally changed unless otherwise specified. The specific example, distribution, numeric values explained in the embodiments are merely examples, and may be optionally changed.

The constituent elements of the devices illustrated in the drawings are merely conceptual, and need not be physically configured as illustrated. The constituent elements, as a whole or in part, can be separated or integrated either functionally or physically based on various types of loads or use conditions. Moreover, the process functions implemented by the devices are entirely or partially implemented by a central processing unit (CPU) or computer programs that are analyzed and executed by the CPU, or implemented as hardware by wired logic.

Hardware

FIG. 16 is a diagram for explaining an exemplary hardware configuration. As illustrated in FIG. 16, the learning device 100 includes a communication device 100a, a hard disk drive (HDD) 100b, a memory 100c, and a processor 100d. Moreover, the constituent elements illustrated in FIG. 16 are connected to each other by a bus.

The communication device 100a is a network interface card and performs communication with other servers. The HDD 100b is used to store computer programs and databases meant for implementing the functions illustrated in FIG. 6.

The processor 100d reads a computer program, which is meant for performing operations identical to the operations of the processing units illustrated in FIG. 6, from the HDD 100b and loads it in the memory 100c; and consequently runs a process for implementing the functions explained with reference to FIG. 6. That is, the process implements functions identical to the processing units of the learning device 100. More particularly, the processor 100d reads, from the HDD 100b, a computer program that enables implementation of functions identical to the learning data generating unit 111, the person-with-medical-history determining unit 112, the weight setting unit 113, the tensor generating unit 114, the learning unit 115, and the predicting unit 116. Then, the processor 100d executes a process that performs operations identical to the learning data generating unit 111, the person-with-medical-history determining unit 112, the weight setting unit 113, the tensor generating unit 114, the learning unit 115, and the predicting unit 116.

In this way, the learning device 100 functions as an information processing device that reads and executes a computer program and thus implements the learning method. Alternatively, the learning device 100 can read the abovementioned computer program from a recording medium using a medium reading device, and can execute the computer program to implement the functions identical to the embodiment described above. Herein, the computer program is not limited to be executed by the learning device 100. Alternatively, for example, even when some other computer or server executes the computer program or even when various such devices execute the computer program in cooperation, the present invention can be implemented in an identical manner.

The computer program can be distributed via a network such as the Internet. Alternatively, the computer program can be recorded in a computer-readable recording medium such as a hard disk, a flexible disk (FD), a compact disk read only memory (CD-ROM), a magneto-optical (MO) disk, or a digital versatile disc (DVD). Then, a computer can read the computer program from the recording medium and execute it.

According to an aspect, it becomes possible to hold down the deterioration in the prediction accuracy.

All examples and conditional language recited herein are intended for pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A non-transitory computer-readable recording medium having stored therein a machine learning and prediction program that causes a computer to execute a process comprising:
    receiving, for each target, attendance record data of an employee as training data that represents source of generation of a tensor including a plurality of elements which multi-dimensionally represent features of the target over a period of time;
    determining whether or not the employee is a person with medical history who has previously taken medical treatment;
    setting, when the employee is the person with medical history, that includes setting a smaller weight to a tensor generated from attendance record data for period of time after period of medical treatment in which the employee had taken medical treatment as compared to weight of a tensor generated from attendance record data for period of time before the period of medical treatment;
    identifying, when the target satisfies a condition, a period of time corresponding to the condition in the training data;
    generating a weighted tensor based on the training data by setting a first weight to a first part of training data corresponding to a first period of time before the specific period of time and setting a second weight different from the first weight to a second part of training data corresponding to a second period of time after the specific time of period;
    first performing tensor decomposition with the weighted tensor serving as input tensor data;
    inputting result of tensor decomposition to a neural network included in a machine learning model;
    second performing training of the neural network; and
    predicting whether or not the target employee for prediction would take medical treatment based on the attendance record data of the target employee for prediction using the trained neural network included in the machine learning model.

2. The non-transitory computer-readable recording medium according to claim 1, wherein,
    the second performing includes calculating, error between an output value, which is output as a result of inputting to the neural network a core tensor that is generated to be similar to a randomly-generated target core tensor at time of the tensor decomposition, and a teacher label, and updating parameters of the neural network and parameters of the tensor decomposition for the target core tensor with use of the error.

3. The non-transitory computer-readable recording medium according to claim 1, wherein the process further comprising:
    setting "0" as weight of the tensor generated from attendance record data for period of time after the period of medical treatment, and
    performing training of the neural network with the tensor serving as the input tensor data.

4. The non-transitory computer-readable recording medium according to claim 2, wherein the process further comprising generating a new core tensor by taking out elements from the updated tensor in such a way that the new core tensor is similar to the updated target core tensor.

5. A machine learning and prediction method comprising:
    receiving, for each target, attendance record data of an employee as training data that represents source of generation of a tensor including a plurality of elements which multi-dimensionally represent features of the target over a period of time;
    determining whether or not the employee is a person with medical history who has previously taken medical treatment;
    setting, when the employee is the person with medical history, that includes setting a smaller weight to a tensor generated from attendance record data for period of time after period of medical treatment in which the employee had taken medical treatment as compared to weight of a tensor generated from attendance record data for period of time before the period of medical treatment, using a processor;
    identifying, when the target satisfies a condition, a period of time corresponding to the condition in the training data, using the processor;
    generating a weighted tensor based on the training data by setting a first weight to a first part of training data corresponding to a first period of time before the specific period of time and setting a second weight different from the first weight to a second part of training data corresponding to a second period of time after the specific time of period, using the processor;
    first performing tensor decomposition with the weighted tensor serving as input tensor data, using the processor;
    inputting result of tensor decomposition to a neural network included in a machine learning model;
    second performing training of the neural network, using the processor; and
    predicting whether or not the target employee for prediction would take medical treatment based on the attendance record data of the target employee for prediction using the trained neural network included in the machine learning model, using the processor.

6. A non-transitory computer-readable recording medium having stored therein a data structure, the data structure comprising:
    a tensor that, when training data that represents source of generation of a tensor including a plurality of elements multi-dimensionally representing features of a target over a period of time satisfies condition, is weighted with respect to the training data by setting a first weight to a first part of training data corresponding to a first period of time before the specific period of time and setting a second weight different from the first weight to a second part of training data corresponding to a second period of time after the specific time of period, and correct-solution information that is assigned to the tensor, wherein tensor decomposition is performed with the weighted tensor serving as input tensor data, the training data is inputting attendance record data of an employee, the condition is determined whether or not the employee is a person with medical history who has previously taken medical treatment, and the period of time is period of medical treatment taken for the employee, the data structure is used in an operation including outputting, from an output layer of a neural network, an output value that represents result of arithmetic operation performed based on a weight coefficient of the neural network when the tensor and the correct-solution information are input as training data to an input layer of the neural network, training the neural network included in a machine learning model by inputting the correct-solution information and the output value, and predicting whether or not the target employee for prediction would take medical treatment based on the attendance record data of the target employee for prediction using the trained neural network included in the machine learning model.

\* \* \* \* \*